US012654012B2

(12) United States Patent
Eskuri

(10) Patent No.: US 12,654,012 B2
(45) Date of Patent: Jun. 16, 2026

(54) NEUROLOGICAL TREATMENT SYSTEM

(71) Applicant: COVIDIEN LP, Mansfield, MA (US)

(72) Inventor: Alan Eskuri, Irvine, CA (US)

(73) Assignee: Covidien LP, Mansfield, MA (US)

( * ) Notice: Subject to any disclaimer, the term of this patent is extended or adjusted under 35 U.S.C. 154(b) by 630 days.

(21) Appl. No.: 17/478,540

(22) Filed: Sep. 17, 2021

(65) Prior Publication Data

US 2022/0001182 A1 Jan. 6, 2022

Related U.S. Application Data

(63) Continuation of application No. 14/019,469, filed on Sep. 5, 2013, now abandoned.

(60) Provisional application No. 61/739,977, filed on Dec. 20, 2012, provisional application No. 61/697,432, filed on Sep. 6, 2012.

(51) Int. Cl.
| *A61N 1/36* | (2006.01) |
| *A61B 17/22* | (2006.01) |
| *A61N 1/05* | (2006.01) |

(52) U.S. Cl.
CPC .......... *A61N 1/36082* (2013.01); *A61B 17/22* (2013.01); *A61N 1/0529* (2013.01); *A61N 1/0551* (2013.01); *A61N 1/36185* (2013.01)

(58) Field of Classification Search
CPC .............. A61N 1/36082; A61N 1/0529; A61N 1/0551; A61N 1/36185; A61B 17/22
See application file for complete search history.

(56) References Cited

U.S. PATENT DOCUMENTS

| 5,167,229 | A | | 12/1992 | Peckham et al. |
| 5,540,736 | A | | 7/1996 | Haimovich et al. |
| 5,591,772 | A | * | 1/1997 | Lane ...................... A61P 29/00 |
| | | | | 549/408 |
| 5,895,416 | A | | 4/1999 | Barreras, Sr. et al. |
| 6,045,532 | A | | 4/2000 | Eggers et al. |
| 6,246,912 | B1 | | 6/2001 | Sluijter et al. |
| 6,332,089 | B1 | | 12/2001 | Acker et al. |
| 6,511,492 | B1 | * | 1/2003 | Rosenbluth ...... A61B 17/22032 |
| | | | | 606/159 |

(Continued)

FOREIGN PATENT DOCUMENTS

| CN | 1929891 A | 3/2007 |
| CN | 102245253 A | 11/2011 |
| WO | 2011002671 A1 | 1/2011 |

OTHER PUBLICATIONS

International Search Report from International Application No. PCT/US2013/058333, mailed Dec. 3, 2013, 5 pp.

(Continued)

*Primary Examiner* — Mark W. Bockelman
(74) *Attorney, Agent, or Firm* — Shumaker & Sieffert, P.A.

(57) ABSTRACT

A neurological treatment apparatus includes a first endovascular device comprising a plurality of first electrodes extending along a first length in a distal portion of the first device, the distal portion of the first device being configured for endoluminal navigation into cerebral vasculature, and a second endovascular device comprising a plurality of second electrodes extending along a second length in a distal portion of the second device, configured for endoluminal navigation into the cerebral vasculature, such that electrostimulative current may be passed between the first and second electrodes.

45 Claims, 6 Drawing Sheets

(56) References Cited

U.S. PATENT DOCUMENTS

| | | | |
|---|---|---|---|
| 6,597,954 B1 | 7/2003 | Pless et al. | |
| 6,757,970 B1 * | 7/2004 | Kuzma | A61N 1/0551 |
| | | | 600/374 |
| 6,871,098 B2 | 3/2005 | Nuttin et al. | |
| 7,010,351 B2 | 3/2006 | Firlik et al. | |
| 7,236,830 B2 | 6/2007 | Gliner | |
| 7,257,439 B2 | 8/2007 | Llinas | |
| 7,286,879 B2 | 10/2007 | Wallace | |
| 7,295,875 B2 | 11/2007 | Wallace et al. | |
| 7,295,880 B2 | 11/2007 | Gielen | |
| 7,519,431 B2 | 4/2009 | Goetz et al. | |
| 7,894,903 B2 | 2/2011 | John | |
| 8,473,059 B2 | 6/2013 | Tass et al. | |
| 8,554,324 B2 | 10/2013 | Brocke | |
| 8,577,470 B2 | 11/2013 | Assaf et al. | |
| 8,615,306 B2 | 12/2013 | Griffith | |
| 9,561,369 B2 | 2/2017 | Burnes et al. | |
| 9,572,982 B2 | 2/2017 | Burnes et al. | |
| 2005/0075679 A1 * | 4/2005 | Gliner | A61N 1/36082 |
| | | | 607/45 |
| 2005/0101860 A1 | 5/2005 | Patrick et al. | |
| 2005/0137647 A1 | 6/2005 | Wallace et al. | |
| 2006/0173493 A1 | 8/2006 | Armstrong et al. | |
| 2006/0217782 A1 * | 9/2006 | Boveja | A61N 1/37235 |
| | | | 607/45 |
| 2007/0021803 A1 | 1/2007 | Deem et al. | |
| 2007/0055332 A1 | 3/2007 | Swoyer | |
| 2007/0106337 A1 | 5/2007 | Errico et al. | |
| 2008/0027346 A1 | 1/2008 | Litt et al. | |
| 2008/0027505 A1 | 1/2008 | Levin et al. | |
| 2008/0046036 A1 | 2/2008 | King et al. | |
| 2008/0215101 A1 | 9/2008 | Rezai et al. | |
| 2008/0312715 A1 | 12/2008 | Asirvatham et al. | |
| 2009/0131738 A1 | 5/2009 | Ferren et al. | |
| 2009/0198172 A1 | 8/2009 | Garrison | |
| 2009/0326607 A1 | 12/2009 | Castel et al. | |
| 2010/0152817 A1 * | 6/2010 | Gillbe | A61N 1/36021 |
| | | | 607/72 |
| 2011/0060212 A1 | 3/2011 | Slee et al. | |
| 2011/0106214 A1 * | 5/2011 | Carbunaru | A61N 1/36125 |
| | | | 607/66 |
| 2012/0059431 A1 | 3/2012 | Williams et al. | |
| 2012/0059437 A1 | 3/2012 | Shalev | |
| 2012/0059438 A1 | 3/2012 | De Ridder | |
| 2012/0078319 A1 | 3/2012 | De Ridder | |
| 2012/0083868 A1 | 4/2012 | Shrivastava et al. | |
| 2012/0136409 A1 | 5/2012 | Goetz et al. | |
| 2012/0158092 A1 | 6/2012 | Thimineur et al. | |
| 2012/0271375 A1 | 10/2012 | Wu et al. | |
| 2012/0316600 A1 | 12/2012 | Ferrera et al. | |
| 2013/0131636 A1 | 5/2013 | Rezai et al. | |
| 2014/0066949 A1 | 3/2014 | Eskuri | |

OTHER PUBLICATIONS

International Preliminary Report on Patentability and Written Opinion from International Application No. PCT/US2013/058333, mailed Mar. 10, 2015, 8 pp.

Second Office Action, and translation thereof, from counterpart Chinese Patent Application No. 201380046455.0, dated Apr. 8, 2016, 18 pp.

Response to Communication pursuant to Rule 161(1) EPC dated Apr. 15, 2015, from counterpart European Application No. 13763405.1, filed Oct. 22, 2015, 3 pp.

Examination Report from counterpart European Application No. 13763405.1, dated Feb. 6, 2018, 4 pp.

First Office Action, and machine translation thereof, from counterpart Chinese Application No. 201380046455.0, dated Sep. 15, 2015, 13 pp.

Third Office Action, and machine translation thereof, from counterpart Chinese Application No. 201380046455.0, dated Jul. 18, 2016, 9 pp.

Notification to Grant, and machine translation thereof, from counterpart Chinese Application No. 201380046455.0, dated Dec. 20, 2016, 16 pp.

Response to Examination Report dated Feb. 6, 2018, from counterpart European Application No. 13763405.1, filed Aug. 6, 2018, 2 pp.

"Alzheimer's vaccine clears amyloid plaques but has little effect on learning and memory impairment," Apr. 7, 2008, http://www.news-medical.net/news/2008/04/07/37012.aspx, 1 pp.

Arendash, "Transcranial Electromagnetic Treatment against Alzheimer's Disease: Why it has the Potential to Trump Alzheimer's Disease Drug Development," IOS Press, Journal of Alzheimer's Disease, Jun. 21, 2012, pp. 1-24.

Baba et al., "Electrical Stimulation of the Cerebral Cortex Exerts Antiapoptotic, Angiogenic, and Anti-Inflammatory Effects in Ischemic Stroke Rates Through Phosphoinositide 3-Kinase/Akt Signaling Pathway," American Heart Association, Stroke, Jul. 23, 2009, pp. e598-e605.

Brushart et al., "Electrical Stimulation Promotes Motoneuron Regeneration without Increasing Its Speed or Conditioning the Neuron," The Journal of Neuroscience, vol. 22, No. 15, Aug. 2002, pp. 6631-6638.

Chang et al., "Electrical stimulation promotes nerve growth factor-induced neurite outgrowth and signaling," BBAGEN 27513, BBA—General Subjects, Apr. 3, 2013, 30 pp.

Cohen et al., "Proliferation of amyloid-B42 aggregates occurs through a secondary nucleation mechanism," Biophysics and Computational Biology, PNAS Early Edition, www.pnas.org/cgi/doi/10.1073/pnas.1218402110, Apr. 2013, 6 pp.

Cramer et al., "ApoE-Directed Therapeutics Rapidly Clear B-Amyloid and Reverse Deficits in AD Mouse Models," Science Mag, Science, vol. 335, Mar. 23, 2012, pp. 1503-1506.

Dolev et al., "Spike bursts increase amyloid-B 40/42 ratio by inducing a presenilin-1 conformational change," Article Preview, Nature Neuroscience, Apr. 7, 2013, 2 pp.

Gasparova et al., "Middle-aged rat hippocampus and some early changes accompanying aging," Versita, Central European Journal of Biology, vol. 7, No. 5, Jun. 18, 2012, pp. 810-816.

Gordon et al., "Brief post-surgical electrical stimulation accelerates axon regeneration and muscle reinnervation without affecting the function measures in carpal tunnel syndrome patients," Elsevier, ScienceDirect, Experimental Neurology, vol. 223, Oct. 1, 2009, pp. 191-202.

Gordon et al., "Augmenting nerve regeneration with electrical stimulation," Maney & Son Ltd., Neurological Research, vol. 30, Dec. 2008, pp. 1012-1022.

Haastert-Talini et al., "Electrical Stimulation Accelerates Axonal and Functional Peripheral Nerve Regeneration across Long Gaps," Journal of Neurotrauma, vol. 28, Apr. 2011, pp. 661-674.

Hardenacke et al., "Stimulate or degenerate Deep brain stimulation of the Nucleus basalis Meynert in Alzheimer's dementia," WNEU 1594, World Neurosurgery, doi: 10.1016/j.wneu.2012.12.005, Dec. 7, 2012, 23 pp.

Heger et al., "USC Team to Use Patch-Clamp, RNA-seq to Study Gene Expression Variability in Single Neurons," Gene Expression Technical Guide, genomeweb.com, Dec. 11, 2012, 3 pp.

JP Morgan, "Medtronic Renal Denervation: The Next Big Thing in Cardiovascular Devices," North America Equity Research, www.morganmarkets.com, Oct. 6, 2011, 28 pp.

Kameda, "Regenerative Medicine for Neurological Diseases with the Use of Electrical Stimulation—Chapter 29," Intech, http:/dx.doi.org/10/5772/55612, (Applicant points out, in accordance with MPEP 609.04(a), that the year of publication, 2013, is sufficiently earlier than the effective U.S. filing date, so that the particular month of publication is not in issue.), 14 pp.

Laxton et al., "DBS for the Treatment of Alzheimer's Disease and Dementias, " WNEU 1337, World Neurosurgery, doi:10.1016/j.wneu.2012.06.028, Jun. 14, 2012, 28 pp.

Liu et al., "Electrical stimulation of cerebellar fastigal nucleus promotes the expression of growth arrest and DNA damage inducible gene B and motor function recovery in cerebral ischemia/reperfusion rats," Elsevier, ScienceDirect, Neuroscience Letters, vol. 520, May 2012, pp. 110-114.

(56)                    References Cited

OTHER PUBLICATIONS

Lowenthal et al., "The Ethics of Early Evidence—Preparing for a Possible Breakthrough in Alzheimer's Disease," The New England Journal of Medicine, vol. 367, No. 6, Aug. 9, 2012, pp. 488-490.

"Medical Device Daily, The Daily Medical Technology News Source," AHC Media, www.MedicalDeviceDaily.com, Aug. 8, 2012, vol. 16, No. 153, Aug. 8, 2012, 13 pp.

"DBS Therapy for Parkinson's Disease and Essential Tremor—Clinical Summary," Medtronic, Inc., (Applicant points put, in accordance with MPEP 609.04(a), that the year of publication, 2009, is sufficiently earlier than the effective U.S. filing date, so that the particular month of publication is not in issue.), 36 pp.

Meloni et al., "Nerve Growth Factor Promotes Cardiac Repair following Myocardial Infarction," American Heart Association, Circulation Research, vol. 106, Apr. 2010, pp. 1275-1284.

Michaud et al., "Toll-like receptor 4 stimulation with the detoxified ligand monophosphoryl lipid A improves Alzheimer's disease-related pathology," Proceedings of the National Academy of Sciences of the United States of America, Dec. 2012, http://www.pnas/org/content/early/2013/01/15/1215165110, 3 pp.

"Poster 208: Patterned Electrical Neuromuscular Stimulation for the Treatment of Dysphagia: Pilot Data," Academy Annual Assembly Abstracts, Arch Phys Med Rehabil vol. 89, Nov. 2008, p. E88.

Reis et al., "Electrical Stimulation of Cerebellar Fastigial Nucleus Reduces Ischemic Infarction Elicited by Middle Cerebral Artery Occlusion in Rat," Raven Press, The International Society of Cerebral Blood Flow and Metabolism, Journal of Cerebral Blood Flow and Metabolism, vol. 11, Mar. 1991, pp. 810-818.

Royo-Gascon et al., "Piezoelectric Substrates Promote Neurite Growth in Rat Spinal Cord Neurons," BMES, Anals of Biomedical Engineering, Aug. 2012, 1 pp.

Royo-Gascon, "Neuroplasticity of Spinal Cord Neurons Based on Piezoelectric Stimulation and Electrophysiological Analysis After Stem Cell-Derived Progenitor Transplant," Dissertation-Rutgers University, Oct. 2011, 142 pp.

Sanganahalli et al., "Functional MRI and neural responses in a rat model of Alzheimer's disease," Elsevier, ScienceDirect, NeuroImage, vol. 79, May 3, 2013, pp. 404-411.

Sharma et al., "New therapeutic advances in CNS injury and repair," 9th global College of Neuroprotection and Neurogeneration (GCNN) Annual Conference, Expert Review Neurotherapeautics, vol. 12, No. 8, May 2012, pp. 901-905.

Smith et al., "Increased Cerebral Metabolism After 1 Year of Deep Brain Stimulation in Alzheimer Disease," Arch Neurol, May 2012, http:/archneur-jamanetwork.com, pp. E1-E8.

Stork et al., "Bursting Oscillations of Neurons and Synchronization," Latest Trends in Circuits, Automatic Control and Signal Processing, http://www.wseas.us/e-library/conferences/2012/Barcelona/CSCS/CSCS-13.pdf, (Applicant points but, in accordance with MPEP 609.04(a), that the year of publication, 2012, is sufficiently earlier than the effective U.S. filing date, so that the particular month of publication is not in issue.), 6 pp.

"WCNR 2012 Poster Abstracts," Sage, Neurorehabilitation and Neural Repair, http://nrr.sagepub.com, (Applicant points out, in accordance with MPEP 609.04(a), that the year of publication, 2012, is sufficiently earlier than the effective U.S. filing date, so that the particular month of publication is not in issue.), 110 pp.

Wu et al., "Effect of deep brain stimulation on subsantia nigra neurons in a rat model of Parkinson's disease," Chinese Medical Journal, vol. 125, No. 22, Apr. 2012, pp. 4072-4075.

Yang et al., "Endovascular Embolization of Distal Anterior Choroidal Artery Aneurysms Associated with Moyamoya Disease—A Report of Two Cases and a Literature Review, " Interventional Neuroradiology, vol. 16, (Applicant points put, in accordance with MPEP 609.04(a), that the year of publication, 2010, is sufficiently earlier than the effective U.S. filing date, so that the particular month of publication is not in issue.), pp. 433-441.

Zhou et al., "Cortical electrical stimulation alone enhances functional recovery and dendritic structures after foal cerebral ischemia in rats," Elsevier, Science Direct, Brain Research 1311, Nov. 24, 2009, pp. 148-157.

Neudorfer et al., "Endovascular deep brain stimulation: Investigating the relationship between vascular structures and deep brain stimulation targets," Elsevier, Brain Stimulation, vol. 13, Oct. 6, 2020, pp. 1668-1677.

Prosecution History from U.S. Appl. No. 14/019,469, dated Sep. 2, 2015 through Sep. 2, 2021, 249 pp.

Advisory Action from U.S. Appl. No. 14/019,469, dated Dec. 6, 2021, 3 pp.

Response to Final Office Action mailed Sep. 2, 2021, from U.S. Appl. No. 14/019,469, filed Nov. 2, 2021, 17 pp.

Response to Office Action dated Mar. 31, 2023 from U.S. Appl. No. 14/019,469, filed Jun. 29, 2023, 11 pp.

Office Action from U.S. Appl. No. 14/019,469 dated Mar. 31, 2023, 19 pp.

Office Action from U.S. Appl. No. 14/019,469, dated Dec. 24, 2021, 19 pp.

Prosecution History from counterpart European Application No. 13763405.1, dated Sep. 10, 2020 through Nov. 9, 2021, 93 pp.

Response to Office Action dated Dec. 24, 2021, from U.S. Appl. No. 14/019,469, filed Mar. 22, 2022, 17 pp.

Final Office Action from U.S. Appl. No. 14/019,469 dated Aug. 5, 2022, 19 pp.

Pre-Appeal Brief Request for Review from U.S. Appl. No. 14/019,469, filed Nov. 3, 2022, 6 pp.

Final Office Action from U.S. Appl. No. 14/019,469 dated Jun. 6, 2024, 25 pp.

Office Action from U.S. Appl. No. 14/019,469 dated Dec. 7, 2023, 24 pp.

Response to Office Action dated Dec. 7, 2023 from U.S. Appl. No. 14/019,469, filed Feb. 21, 2024, 18 pp.

Advisory Action from U.S. Appl. No. 14/019,469 dated Aug. 19, 2024, 3 pp.

Response to Final Office Action dated Jun. 6, 2024 from U.S. Appl. No. 14/019,469, filed Aug. 6, 2024, 15 pp.

* cited by examiner

NEUROLOGICAL TREATMENT SYSTEM

RELATED APPLICATIONS

The present application is a continuation of U.S. patent application Ser. No. 14/019,469, filed on Sep. 5, 2013, which claims the benefit of each of U.S. Pat. App. Ser. No. 61/697,432, filed on Sep. 6, 2012, and U.S. Pat. App. Ser. No. 61/739,977, filed on Dec. 20, 2012. The entire contents of each of the above referenced applications is incorporated by reference, as if fully set forth herein.

FIELD

The present disclosure relates to neurological treatment. In particular, the present disclosure relates to neurological treatment by electrostimulation along pathways within brain tissue.

BACKGROUND

Neurodegenerative diseases and their effects can include Alzheimer's Disease, Parkinson's disease, Huntington's disease, tremor, epilepsy, and/or ischemia of the brain, such as stroke. These may include or lead to progressive loss of structure or function of neurons, including death of neurons.

SUMMARY

The subject technology is illustrated, for example, according to the following non-limiting summary of some embodiments disclosed herein. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

Clause 1. A method, comprising:
inserting a first endovascular device within a first cerebral blood vessel, the first endovascular device comprising a plurality of first electrodes extending along a first length in a distal portion of the first device;
inserting a second endovascular device within a second cerebral blood vessel, the second endovascular device comprising plurality of second electrodes extending along a second length in a distal portion of the second device;
passing electrical currents along a plurality of pathways between the first electrodes and the second electrodes, wherein at least a portion of the pathways pass through at least one of the hippocampus or dentate gyrus.

Clause 2. The method of clause 1, wherein inserting the second endovascular device comprises placing the second electrodes on a side of the hippocampus or dentate gyrus opposite the first electrodes.

Clause 3. The method of clause 1, wherein passing electrical currents comprises passing said currents between a plurality of said first electrodes and a plurality of said second electrodes.

Clause 4. The method of clause 1, wherein said currents comprise neurostimulative currents.

Clause 5. An apparatus comprising:
a first endovascular device comprising a plurality of first electrodes extending along a first length in a distal portion of the first device, the distal portion of the first device being configured for endoluminal navigation into cerebral vasculature;
a second endovascular device comprising a plurality of second electrodes extending along a second length in a distal portion of the second device, the distal portion of the second device being configured for endoluminal navigation into cerebral vasculature;
a power source in electrical communication with the first electrodes and the second electrodes;
a controller in communication with the power source; and
a machine-readable medium comprising instructions executable by the controller to operate the power source so as to establish a network of neurostimulation current pathways between the first electrodes and the second electrodes.

Clause 6. The apparatus of clause 5, wherein:
one of said endovascular devices comprises a proximally located electrode;
the other of said endovascular devices comprises a distally located electrode; and
said network includes at least one neurostimulation current pathway between said proximally located electrode and said distally located electrode.

Clause 7. The apparatus of clause 5, wherein said network comprises first neurostimulation pathways that extend mainly or only laterally, and second neurostimulation pathways that extend both laterally and longitudinally.

Clause 8. The apparatus of clause 5, wherein said algorithm is executable by the controller to operate the power source so as to pass neurostimulative electrical current along said current pathways.

Clause 9. The apparatus of clause 8, wherein said electrical current is configured to regenerate neurocytes in the tissue through which said network passes.

Clause 10. An apparatus comprising:
a first endovascular device comprising a plurality of first electrodes extending along a first length in a distal portion of the first device, the distal portion of the first device being configured for endoluminal navigation into cerebral vasculature;
a second endovascular device comprising a plurality of second electrodes extending along a second length in a distal portion of the second device, the distal portion of the second device being configured for endoluminal navigation into the cerebral vasculature; and
means for passing electrostimulative current between the first electrodes and the second electrodes.

Clause 11. The apparatus of clause 10, wherein said means further comprises means for establishing a network of neurostimulation current pathways between the first electrodes and the second electrodes.

Clause 12. The apparatus of clause 11, wherein said network comprises first neurostimulation pathways that extend mainly or only laterally, and second neurostimulation pathways that extend both laterally and longitudinally.

Clause 13. The apparatus of clause 10, wherein said means comprises a controller and program instructions accessible by said controller.

Clause 14. The apparatus of clause 10, wherein said means is configured for at least one of:
regenerating cerebral neurocytes;
inhibiting or reversing the formation of neurofibrillary tangles;
inhibiting or reversing the formation of amyloid plaques;
inhibiting or reversing the attachment of amyloid plaques to neurocytes;

inhibiting the cellular apoptosis cascade associated with ischemic stroke; or increasing rate and volume of pharmacologic agent delivery.

Clause 15. A method, comprising:

providing a first treatment to increase blood flow downstream of an obstruction at an obstruction location within a blood vessel of a patient;

inserting a first endovascular device downstream of the obstruction location, the first endovascular device comprising a plurality of first electrodes extending along a first length in a distal portion of the first device;

inserting a second endovascular device downstream of the obstruction location, the second endovascular device comprising plurality of second electrodes extending along a second length in a distal portion of the second device;

passing electrical currents along a plurality of pathways between the first electrodes and the second electrodes, wherein at least a portion of the pathways pass through a region of brain tissue affected by the obstruction.

Clause 16. The method of clause 15, wherein the first treatment comprises mechanically removing, lysine, breaking up, or aspirating the obstruction.

Clause 17. The method of clause 15, wherein the first treatment comprises administering a blood thinner to the patient.

Clause 18. The method of clause 15, wherein inserting the first endovascular device comprises inserting the first endovascular device into a first blood vessel downstream of the obstruction location.

Clause 19. The method of clause 18, wherein inserting the second endovascular device comprises inserting the second endovascular device into a second blood vessel, different from the first blood vessel, downstream of the obstruction location.

Clause 20. The method of clause 15, wherein the region of brain tissue affected by the obstruction comprises an infarction.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

In the following detailed description, numerous specific details are set forth to provide a full understanding of the subject technology. However, the subject technology may be practiced without some of these specific details. In other instances, well-known structures and techniques have not been shown in detail so as not to obscure the subject technology.

Figure 1:
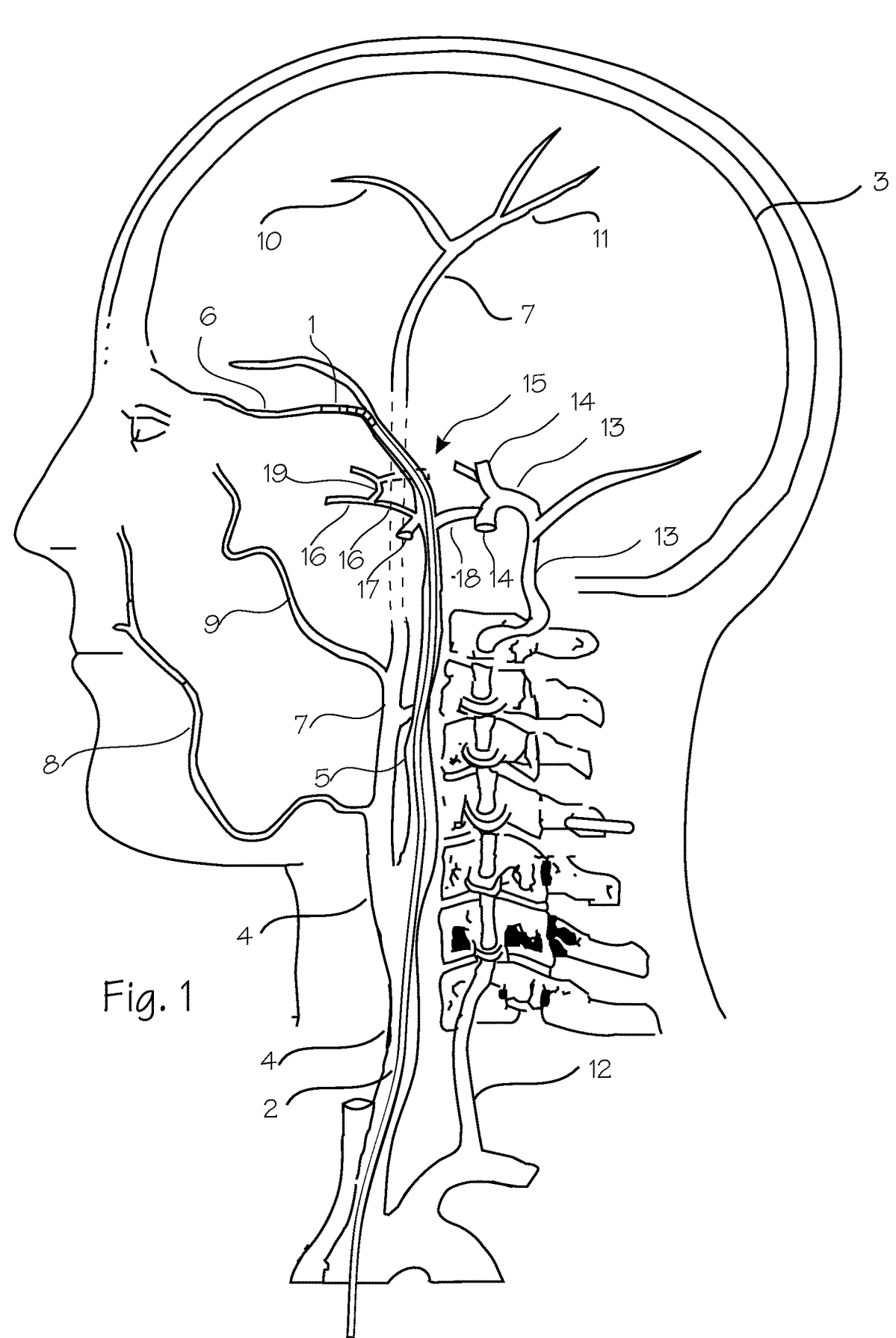
FIG. 1 is a schematic view of a vasculature of a brain.

FIG. 1 shows the vasculature of the brain. The brain 3 is supplied with blood through the carotid and the vertebral arteries on each side of the neck. The arteries include the common carotid artery 4 in the neck, which is a common access pathway for the various devices and/or methods disclosed herein, the internal carotid 5 which supplies the ophthalmic artery 6. The external carotid 7 supplies the maxillary artery 8, the middle meningeal artery 9, and the superficial temporal arteries 10 (frontal) and 11 (parietal). The vertebral artery 12 supplies the basilar artery 13 and the cerebral arteries including the posterior cerebral artery 14 and the circle of Willis indicated generally at 15. The siphon of the vertebral artery appears in the intra-cranial vasculature on the vertebral approach to the Circle of Willis. Also supplied by the internal carotid artery are the anterior cerebral artery 16 and the middle cerebral artery 17, as well as the circle of Willis, including the posterior communicating artery 18 and the anterior communicating artery 19. The siphon of the internal carotid artery 5 appears in the intra-cranial vasculature on the carotid approach into the Circle of Willis. These arteries typically have an internal diameter of about 1 mm to 5 mm, most commonly from 2-4 mm. The methods and devices described herein allow access to these arteries for treatment(s). In FIG. 1, an insertion catheter 2 (which can comprise, for example, a microcatheter) is shown extending through the common carotid artery 4 and the internal carotid artery 5, with a device 1 extending through the catheter 2 and into the anterior cerebral artery 16.

Figure 2:
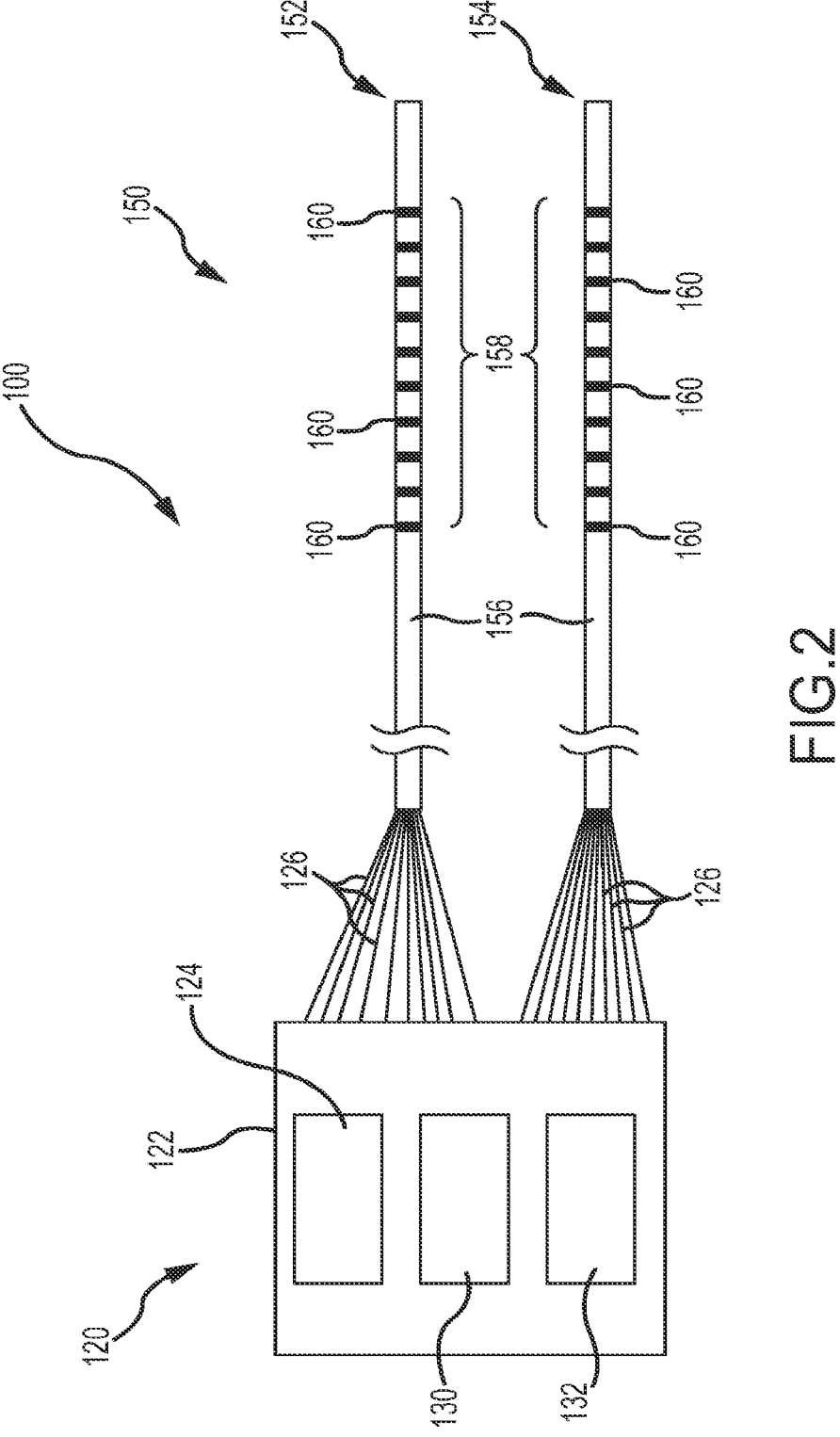
FIG. 2 is a schematic view of a neurological treatment system.
Figure 3A:
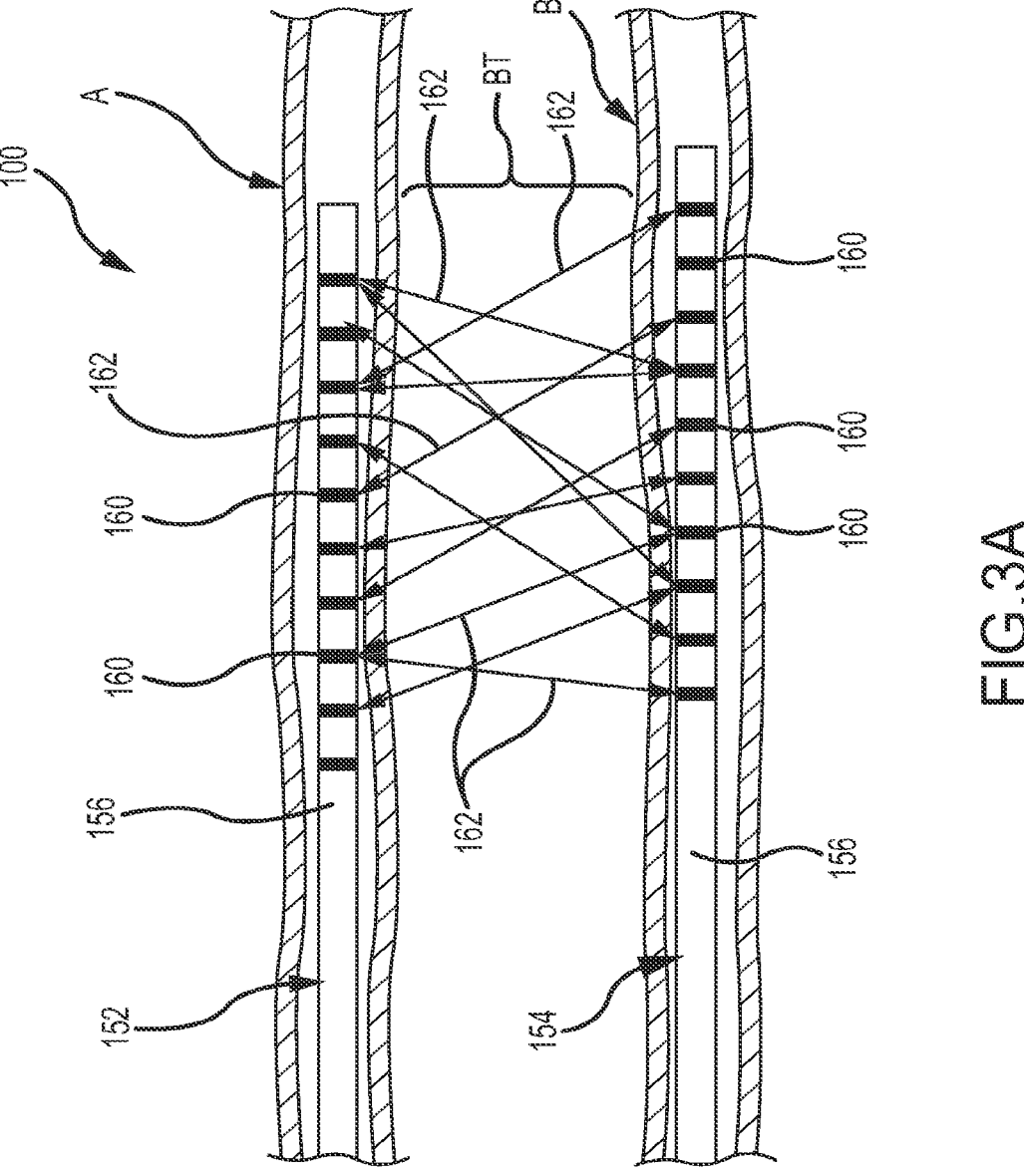
FIG. 3A is a schematic view of the neurological treatment system of FIG. 2 and a method of using the system to treat brain tissue.
Figure 3B:
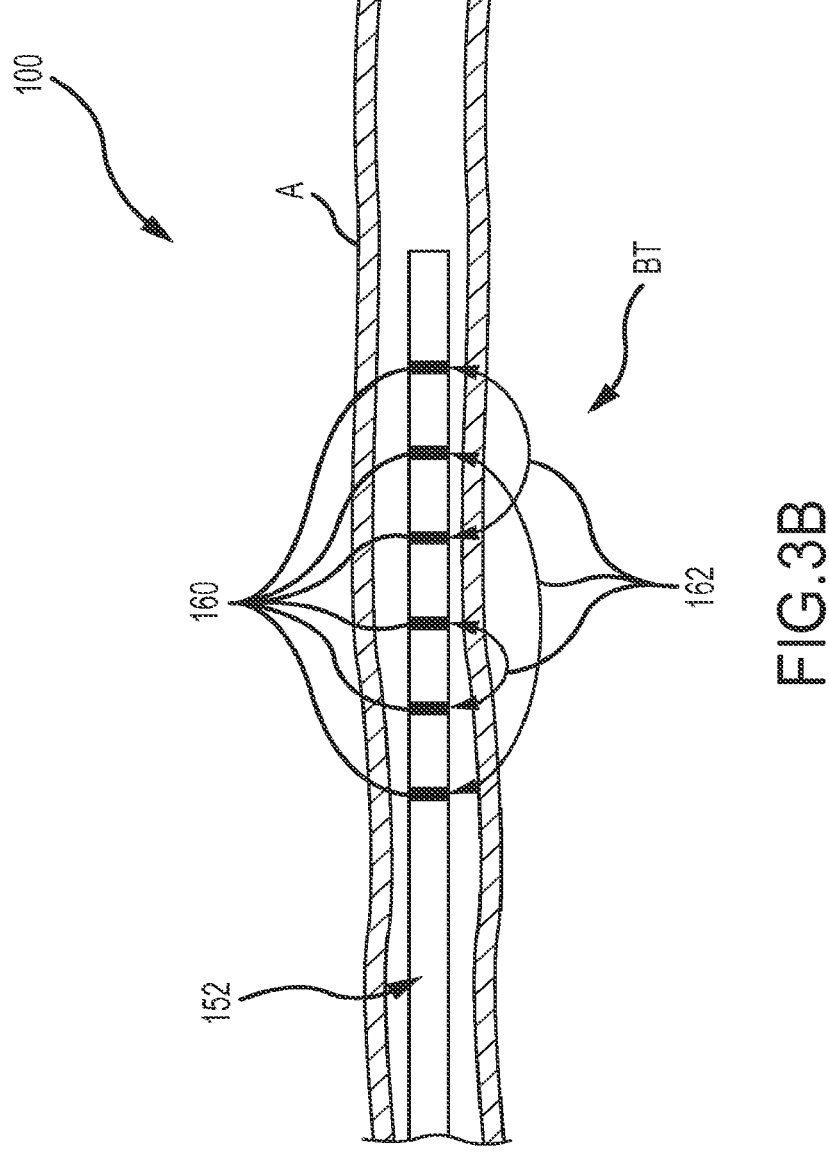
FIG. 3B is a schematic view of a neurological treatment system and a method of using the system to treat brain tissue.

FIGS. 2 and 3A-3B depict a neurological treatment system 100 that can be used to treat neurological disorders such as Alzheimer's disease by applying energy to the affected tissue, such as brain tissue and/or other neurological tissues. The system 100 can comprise an energy generation portion 120 that is coupled or configured to be coupled to an energy application portion 150, so that energy developed by the generation portion 120 can be transmitted to, and applied to tissue by, the application portion 150.

In one embodiment, the energy generation portion 120 can comprise an electrical generator 122 configured to output medically useful electrical current, which can be electrostimulative, electrosurgical and/or ablative current. The generation portion 120 can include a suitable controller 124 that can be used to control various parameters of the energy output by the portion 120/generator 122, such as intensity, amplitude, duration, frequency, duty cycle, polarity, etc. The energy application portion 150 can comprise one or more endovascular devices (such as the depicted pair of first and second endovascular devices 152, 154), or an endovascular device and an extracorporeal conductive device such as a grounding pad.

One or both of the endovascular devices 152, 154 can comprise an elongate, flexible shaft 156 that is sized and configured for navigation through blood vessels such as cerebral blood vessels. The shaft 156 can be a tube or other elongate member formed from a flexible, preferably electrically insulative material. Suitable materials for the shaft 156 include medically acceptable polymers, or metals (e.g. in the form of a hypotube) coated with a suitable electrical insulator, or combinations thereof. The endovascular devices 152, 154 can each further comprise an energy application region 158 which can in turn comprise one or more (e.g., 1, 2, 3, 4, 5, 8, 10, 12, 15, or 20 or more) electrodes 160. The devices 152, 154 can each have the same number of electrodes, or the device 152 can have a number of electrodes 160 that is different from the number of electrodes of the device 154.

The electrodes 160 can comprise metallic or other conductive rings, or coils or other suitable conductive structures, and can each form an outer conductive surface that is exposed and configured for electrically conductive contact with adjacent tissue, such as the inner wall of a blood vessel, and/or brain tissue or other neurological tissue being treated by the system 100. Some or all of the outer conductive surfaces can extend partially or completely circumferentially around the longitudinal axis of the endovascular device 152/154. The outer conductive surfaces can be approximately flush with the outer surface of the shaft 156, or they can extend radially outward from the outer surface of the shaft 156, e.g. in a bulged or toroidal shape. The electrodes 160 can have a fixed outer diameter or size, or a radially expandable outer diameter or size. One, some, or all of the electrodes 160 can be "painted" electrodes.

During use, one or both of the endovascular devices 152, 154 can be employed to apply energy to the tissue being treated. For example, FIG. 3A schematically depicts the use of both endovascular devices 152, 154 to treat brain tissue BT, which can be located within a cranium. To facilitate treatment of the brain tissue BT, the devices 152, 154 can be inserted into or otherwise located in blood vessels A, B, which can be cerebral, intracranial, pericranial, and/or neurovascular blood vessels. Alternatively, one or both of the devices 152, 154 can be inserted or implanted directly into the brain tissue BT.

After insertion, one or both of the devices 152, 154 can be energized to apply energy to the brain tissue BT. For example, one or more, or all, of the electrodes 160 of the first endovascular device 152 can be energized and pass electrical current to one or more, or all, of the electrodes 160 of the second endovascular device 154. This can be accomplished by activating a current source (e.g. the generator 122) connected to the energized electrode(s) of the first endovascular device 152 by leads 126, or activating those portions of the current source 122 that are connected to the energized electrode(s), and/or at least temporarily (e.g. electronically via the controller 124) switching the energized electrode(s) into electrical communication with the current source 122 or the activated portion(s) thereof. While the electrode(s) 160 of the first device 152 are energized in this manner to thereby serve as "active" electrode(s), one or more of the electrodes 160 of the second device 154 can be connected to ground and thereby serve and ground electrodes that receive current propagating from the active electrode(s). This can be accomplished by at least temporarily (e.g. electronically via the controller 124) switching the selected ground electrode(s) into electrical communication with ground, or simply leaving the selected ground electrodes in electrical communication with ground throughout the desired treatment period. One or more electrode pairs can thereby be formed between at least one active electrode and at least one ground electrode, and electrical current 162 passed across the electrode pair from the active to the ground electrode.

During operation, in one embodiment, each electrode 160 of both endovascular devices 152, 154 can be bifunctional; that is, each electrode 160 can serve as either an active electrode or a ground electrode at different points in time as the treatment proceeds. Electrode pairs can be established temporarily and the constituent electrodes selected randomly or in a preset pattern to form a large variety of conduction pathways or currents 162 during the treatment cycle. For example, an electrode pair can be formed temporarily from a relatively distally located electrode 160 of the second device 154 (serving, e.g., as the active electrode) and a relatively proximally located electrode 160 of the first device 152 (serving, e.g., as the ground electrode), thereby creating a pathway or current 162 that traverses both longitudinally and laterally through the brain tissue BT, from the second device 154 to the first device 152. Instead of or in addition to currents/pathways of this type, electrode pairs can be formed from electrodes that are longitudinally closer together, so that the resulting current traverses mainly or only laterally through the brain tissue BT. If desired, during the period of time that a given electrode pair is formed, the polarity can be switched once or repeatedly, to create currents traveling in either direction along the pathway.

Preferably, during operation the system 100 uses all (or a large proportion) of the available current pathways at various times during the treatment cycle. Thus is formed a relatively dense "stimulation matrix" or network as depicted by the current pathways in FIG. 3A, and a relatively large proportion of the volume of the treated tissue BT is located on or near a conduction pathway 162, as the system 100 sequentially or simultaneously activates a large selection of available electrode pairs during the treatment period. For example, a first pair of electrodes 160 may form a pathway 162 in a first operation. Subsequently, a second pair of electrodes 160, different from the first pair of electrodes 160, may form a different pathway 162 in a second operation. Alternatively or in combination, a first pair of electrodes 160 and the second pair of electrodes 160 may form respective pathways 162 simultaneously.

The controller 124 or other suitable hardware can execute an algorithm or program instructions, stored in memory accessible by the controller 124, to activate electrode pairs or sets in a sequence that is preset, random or otherwise. The controller 124 may provide a module for executing such an algorithm or program instructions. Further provided are a processor 130 for executing instructions and a machine-readable medium 132, such as a volatile or non-volatile memory, for storing data and/or instructions. The instructions, which may be stored in a machine-readable medium, may be executed by the controller 124.

Where the first and second device 152, 154 contain X and Y electrodes, respectively, the devices collectively form 2XY possible conduction pathways (comprising only one electrode from the first device and only one electrode from the second device), taking into account that each conduction pathway can operate in two directions or polarities. Preferably, the algorithm or program instructions call for use of all, or significantly more than half, of the 2XY available pathways during a single treatment period with the system 100. In various embodiments, X and Y can each be greater than or equal to 5, or greater than or equal to 10, or any other suitable number or range disclosed herein.

As shown in FIG. 3B, instead of or in addition to the "two-device" pathways depicted in FIG. 3A, "single-device" pathways may be formed and employed, using two or more electrodes 160 on a single device 152 to form an electrode pair or set and pathway 162 through brain tissue BT. In any operation of the system 100, one or both devices 152, 154 can be moved or reciprocated longitudinally within the treated tissue (e.g. brain tissue BT) to move the resulting conduction pathways within the tissue, increasing the proportion of treated tissue.

The current 162 applied by the system 100 can be any suitable therapeutic current. For example, the current 162 can be electrostimulative current, and the generator 122 can comprise an electrostimulation generator. Where the treated tissue comprises the brain tissue BT, any electrostimulation current suitable for brain tissue can be employed. Other suitable therapeutic current includes radiofrequency current, or any therapeutic or ablative alternating or direct current. Instead of or in addition to the electrodes 160, suitable antennae may be employed on the device(s) 152, 154 to apply microwave energy to the treated tissue. Alternatively, the device(s) 152, 154 can be configured to direct light energy (e.g. infrared laser) into or through the desired treated tissue. Multiple such emitters, for example, fiber optics, can be arranged in an array similar to the electrode arrays shown in FIGS. 2 and 3A-3B. The laser wavelength can be selected to either propagate through or be absorbed by the treated tissue, to a desired degree in either case.

When the system 100 is employed to treat Alzheimer's disease, the treated brain tissue BT can comprise the hippocampus and/or dentate gyrus, and the devices 152, 154 (e.g., the electrodes 160 thereof, or other energy emitters) can be inserted into vascular locations near either such structure, e.g. in vascular locations on opposite sides of either structure. For example, the devices 152, 154 can be inserted into the cerebral arteries (i.e., Posterior, Middle, Anterior and/or Basilar), and then employed to apply energy, such as electrostimulative current as described above and/or depicted in FIGS. 3A-3B to the hippocampus and/or dentate gyrus. Thus, the applied electrostimulative current can take the form of neurostimulative current, including any such current that is suitable for regenerating cerebral neurocytes. The applied current can therefore treat Alzheimer's disease by regenerating cerebral neurocytes, and/or inhibiting or reversing the formation of neurofibrillary tangles or amyloid plaques, in the treated area. In one embodiment, a method comprises administering to a patient electrostimulative or neurostimulative current using any apparatus or technique disclosed herein.

The device(s) 152, 154 can be delivered to and/or through any one or more of a number of vessels to access a treatment region. One or more blood vessels may be utilized to reach the target region. The device(s) 152, 154 may span, straddle, or encompass a treatment region based on location within one or more blood vessels.

The device(s) 152, 154 can stimulate the cortex of the brain or the deep brain to provide post-stroke rehabilitation (from hemorrhagic stroke, ischemic stroke or head/brain trauma), Parkinson's disease, essential tremor, Huntington's disease, Alzheimer's disease, epilepsy, depression, obsessive compulsive disorder, schizophrenia, and neuropathic pain. Any lobe of the cortex or deep brain can be stimulated, for example, the cortical region of the brain, the motor strip, sensor strip, and/or premotor cortex, inter alia. Examples of arteries providing access to the cortex include any of the branches off of the external carotid, maxillary, or meningeal arteries. Examples of veins providing access to the cortex include the superior sagittal sinus, any of the superior cerebral veins branching from the superior sagittal sinus (e.g., the lacuna, frontopolar vein, anterior frontal vein, posterior frontal vein, precentral vein, central vein, anterior parietal vein, posterior parietal vein, and occipital vein), superior sylvian vein, vein of Labbe, vein of Trolard, inferior sagittal sinus, and any inferior cerebral veins branching off of the inferior sagittal sinus, transverse sinus, and meningeal sinus.

The device(s) 152, 154 can stimulate the deep brain region by accessing the anterior thalamus, ventrolateral thalamus (Thal), internal segment of globus pallidus (GPi), substantia nigra pars reticulata (SNr), subthalamic nucleus (STN), external segment of globus pallidus (GPe), neostriatum, cingulate, and cingulate gyms, inter alia. Examples of arteries providing access to the deep brain include any branches off of the internal carotid or vertebral arteries. Examples of veins providing access to the deep brain include the inferior sagittal sinus, pericallosal sinus, cavernous sinus, sphenoid sinus, temperal basal vein, and occipital veins.

The device(s) 152, 154 can stimulate the spheno palatine ganglion (SPG), which can control the amount of blood flow to the brain and the permeability of the blood brain barrier, e.g., to hyperperfuse a hemisphere of the brain damaged as a result of an ischemic event, such as a stroke, or to help metabolize amlyoid plaques caused by Alzheimer's Disease and prevent the occurrence of vaso-spasms, both achieved through increased blood flow to the brain. Examples of arteries providing access to the SPG include the maxillary artery, descending palatine artery, and facial artery. Examples of veins providing access to the SPG include the superficial temporal veins and the facial vein.

The various embodiments of the system 100 disclosed herein can be employed in still further applications. For example, any of the disclosed embodiments of the system 100 can be employed to promote local uptake or tissue diffusion of vascularly delivered pharmacologic or biologic agents. To accomplish this, the system 100 (particularly the electrodes 160 of the device(s) 152, 154) can be employed to establish or maintain an electrical field in the presence of a pharmacologic or biologic agent, and thereby enhance the uptake and/or tissue diffusion of the agent(s). This can be performed in brain tissue BT as described in connection with FIGS. 3A-3B, or in other types of tissue. The electrical field established or maintained with the system 100 can be of an intensity that induces electro-permeation of the blood-brain barrier, e.g. at an intensity below that which induces electroporation. According to the above-disclosed methods, the various embodiments of the system 100 can be employed to enhance drug delivery through electropermeation of barrier tight junctions.

The various disclosed embodiments of the system 100 can also be used to accelerate neural stem cell differentiation and/or activation, e.g. into a functional network. The system 100 can be activated to electrically stimulate undifferentiated stem cells and induce potentiation to neurons. The system 100 can also be employed to electrically stimulate implanted pluripotent stem cells or previously cultured neurons, and cause them to populate and connect into functioning neural networks faster or more efficaciously. When used for the purposes described in this paragraph, the system 100 can be deployed, e.g. as described in connection with FIGS. 3A-3B, to provide endovascular or transvascular electrical stimulation to stem cells, cultured neurons or a combination of the two. In this manner the system can provide neurological therapy by enhancing or accelerating the formation or repair of neural networks.

The disclosed embodiments of the system 100 can also be used to heal, enhance or repair neural tissue by accelerating myelin sheath formation. For example, the system 100 can be deployed endovascularly into neural tissue, e.g. as described in connection with FIGS. 3A-3B, and be activated to electrically stimulate myelin sheath repair or formation in the targeted neural tissue. This may be done in a patient suffering from degenerated or ungenerated myelin sheaths.

The disclosed embodiments of the system 100 can also be used to inhibit the apoptosis cascade associated with ischemic stroke. For example, the system 100 can be deployed endovascularly into neural tissue, e.g. as described in connection with FIGS. 3A-3B, and be activated to electrically stimulate infarcted areas of targeted tissue. In this manner, the system 100 can inhibit the amount of neurological decline associated with ischemic stroke.

With reference to FIGS. 4A-4D, the disclosed embodiments of the system 100 can be used as a secondary treatment in conjunction with a primary treatment, such as mechanical thrombectomy and/or blood thinners. A primary treatment may be adapted to address conditions including deep vein thrombosis, pulmonary embolism, myocardial infarction, and stroke. For example, a stroke may be treated by restoration of blood flow and/or by removal of a thrombus or other obstruction in a blood vessel. Mechanical thrombectomy devices include any device capable of removing, lysing, breaking up, and/or aspirating a thrombus or other obstruction. Mechanical thrombectomy devices, such as stentrievers, may be employed to address a cause of an ischemic stroke. Examples of some mechanical thrombectomy devices and methods are disclosed in U.S. Pub. No. 2011/0060212, published on Mar. 10, 2011, and U.S. Pub. No. 2012/0083868, published on Apr. 5, 2012, and U.S. Pub. No. 2012/0316600, published on Dec. 13, 2012, the entire contents of each of which are incorporated herein by reference. Alternatively or in combination with the above, an aspiration device may be provided to remove a thrombus or other obstruction from a blood vessel by aspiration. Alternatively or in combination with the above, a drug therapy may be applied as a primary stroke treatment. For example, blood thinners (e.g., anticoagulants) may be provided to treat an ischemic stroke or enhance performance of a mechanical thrombectomy device. A primary treatment may be applied to address an obstruction at or near an internal carotid artery (ICA), a middle cerebral artery (MCA), an M1 bifurcation, a vertebral artery, a basilar artery or bifurcation, or other location in a vasculature.

Figure 4A:
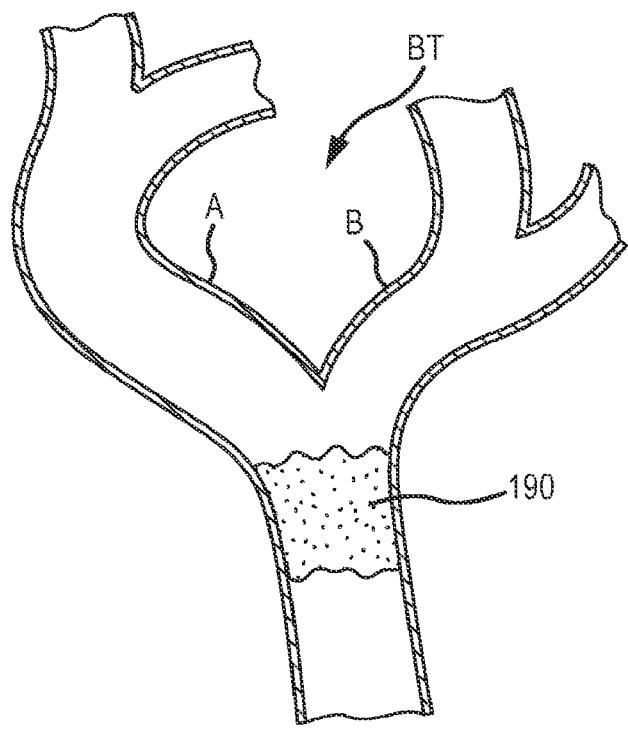
FIG. 4A is a schematic view of an obstructed blood vessel and a stage of a method of using the neurological treatment system of FIG. 2 to treat brain tissue.
Figure 4B:
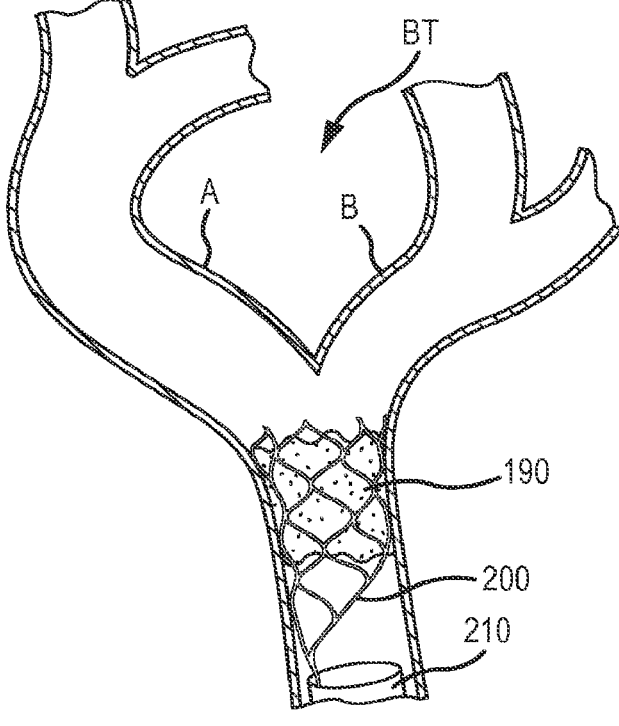
FIG. 4B is a schematic view of a mechanical thrombectomy device and a stage of a method of using the neurological treatment system of FIG. 2 to treat brain tissue.

As shown in FIG. 4A, an obstruction 190 partially blocks blood flow to each of the blood vessels A, B. The brain tissue BT near or between the blood vessels A, B may be affected by the obstruction 190. As shown in FIG. 4B, an exemplary mechanical thrombectomy device 200 (such as a stentriever and/or any other suitable mechanical thrombectomy device(s)) may be deployed from a catheter 210 to treat the obstruction 190. The obstruction 190 is removed, lysed, broken up, and/or aspirated.

Figure 4C:
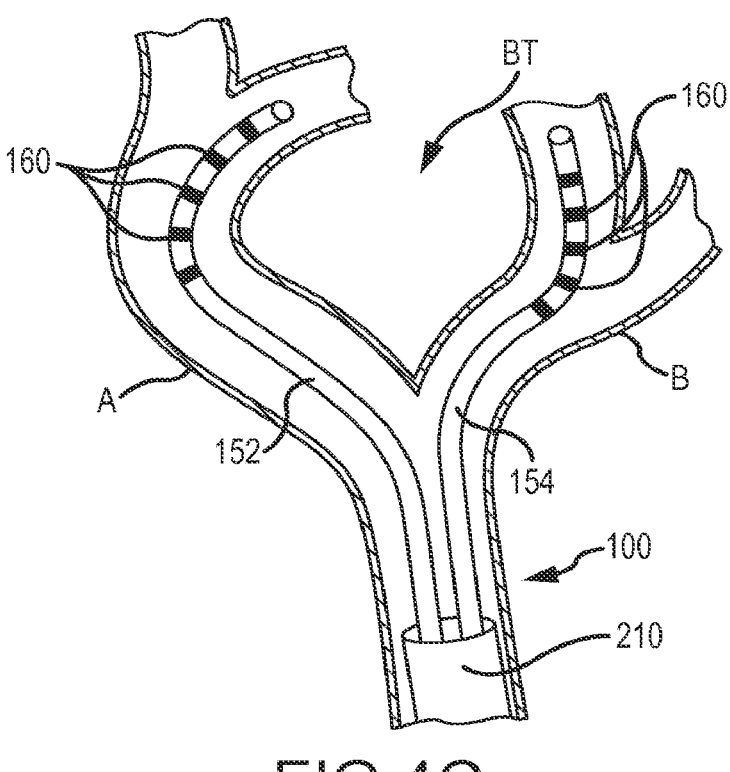
FIG. 4C is a schematic view of the neurological treatment system of FIG. 2 and a stage of a method of using the system to treat brain tissue.
Figure 4D:
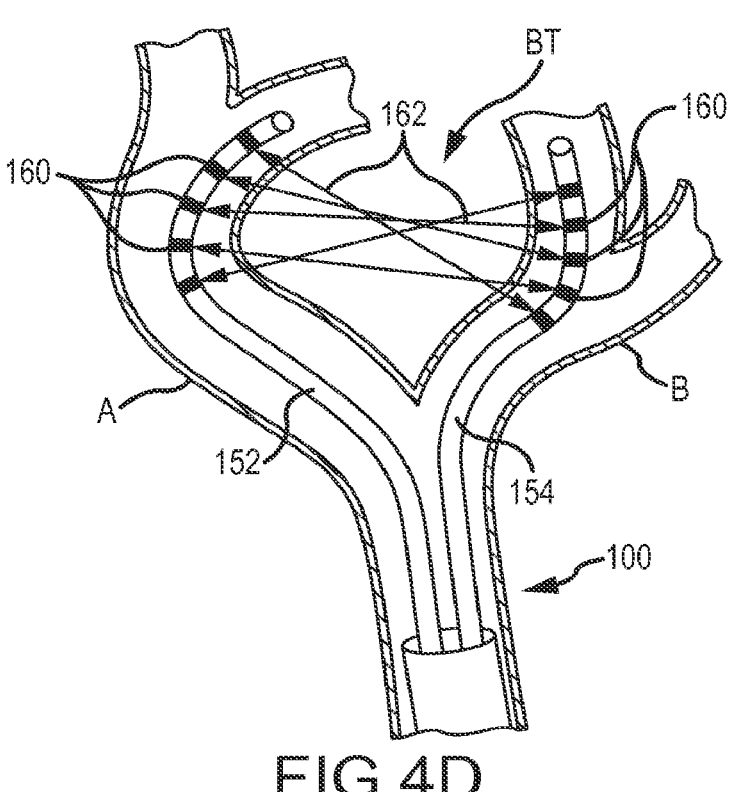
FIG. 4D is a schematic view of the neurological treatment system of FIG. 2 and a stage of a method of using the system to treat brain tissue.

As shown in FIG. 4C, a secondary treatment employing the disclosed embodiments of the system 100 may be applied, and can comprise operating the system 100 in any manner or method disclosed herein. For example, the devices 152, 154 may be navigated from the catheter 210 or another catheter through the blood vessels A, B so as to encompass an affected region of the brain tissue BT. The blood vessels A, B may be downstream of the location of the obstruction 190. The affected region of the brain tissue BT may have suffered an infarction, acute hypoxia, or be otherwise affected by inadequate blood flow during the stroke. As shown in FIG. 4D, one or more pathways or currents 162 are provided in the brain tissue BT between the electrodes 160 of the device 152 and the electrodes 160 of the device 154. While two devices 152, 154 are shown, the use of only one device 152 is also contemplated according to embodiments disclosed herein.

Operation of the device(s) 152, 154 provides stimulation to the affected region. For example, based on the location of an obstruction, a target region downstream of the location of the obstruction is identified. The target region of the brain tissue BT may be one or more of the brainstem, the cerebral cortex, the cerebellum, the parietal lobe, the temporal lobe, the frontal lobe, the spinothalamic tract, corticospinal tract, the dorsal column, the motor cortex, the sensory cortex, Wernicke's area, Broca's area, or any other region affected by a stroke. One or both of the device(s) 152, 154 are navigated vascularly to at least partially encompass the target region affected by the stroke. For example, one or both of the device(s) 152, 154 may be navigated to be near or encompass an affected region at, near, or downstream of an internal carotid artery (ICA), a middle cerebral artery, an M1 bifurcation, a vertebral artery, or a basilar artery or bifurcation. One or both of the device(s) 152, 154 may be navigated through the blood vessel in which the obstruction occurred. One or both of the device(s) 152, 154 provides stimulation to one or more affected regions to inhibit an amount of neurological decline associated with the stroke.

A secondary treatment employing the disclosed embodiments of the system 100 may be applied prior to, during, and/or after a primary treatment. A secondary treatment may be applied during the same procedure in which a primary treatment is employed. For example, the device(s) 152, 154 may provide a stimulation treatment for a period of time following reperfusion of a blood vessel. The stimulation may promote growth factors, thereby stimulating cellular growth. Applying a stimulation treatment immediately or otherwise after reperfusion can decrease the severity of a stroke, thereby reducing complications and cost associated with further recovery. Alternatively or in combination with the above, a secondary treatment employing the disclosed embodiments of the system 100 may be applied in a (second, third, fourth, etc.) procedure apart from the (first) procedure in which a primary treatment is employed. For example, the second, third, fourth and/or any other such subsequent procedure can be performed on a different day, and/or in a different week, month, or year from the first procedure.

While a secondary treatment may supplement a primary treatment for stroke, the disclosed embodiments of the system 100 can be used with other primary treatments to address conditions including deep vein thrombosis, pulmonary embolism, and myocardial infarction. In each case, a secondary treatment employing the disclosed embodiments of the system 100 may be performed prior to, during, or after a primary treatment of the condition (e.g., deep vein thrombosis, pulmonary embolism, and myocardial infarction). A target region affected by the condition is identified and stimulated.

A primary treatment may be applied to address other conditions, such as atherosclerosis, vasoconstriction, artery dissection, vasculopathy, Moyamoya disease, fibromuscular dysplasia, arterial embolus, and intracerebral hemorrhage.

Corresponding primary treatments may be provided in conjunction with a secondary treatment employing the disclosed embodiments of the system 100.

The disclosed embodiments of the system 100 can be used to treat the effects of traumatic brain injury. Rapid acceleration or deceleration of the head can result in the corpus callosum shearing against the falx cerebri. The stimulation provided by the system 100 may promote growth factors, thereby stimulating cellular growth. Applying a stimulation treatment after traumatic brain injury may reduce the severity of its effects.

An exemplary treatment of the present disclosure has a duration of approximately one hour, or less than approximately one hour. For example, a treatment may include applying stimulation for about 10, 20, 30, 40, 50, 60, 70, 80, 90, 100, 110, or 120 minutes. A treatment session may be repeated multiple times with consistent or varied frequency within a given time period. For example, a treatment may be applied one or more times in a day, one or more times in a week, one or more times in a month, or one or more times in a year. An interval between consecutive treatment sessions may be one or more days, one or more weeks, one or more months, or one or more years.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A method comprising:

transmitting, via a plurality of first electrodes of a first endovascular device within a first blood vessel proximate a target brain tissue site of a patient or a plurality of second electrodes of a second endovascular device within a second blood vessel proximate the target brain tissue site, electrical stimulation along a plurality of conduction pathways that intersect each other to the target brain tissue site during a treatment cycle to establish, during the treatment cycle, a network of the conduction pathways between the plurality of first electrodes and the plurality of second electrodes; and receiving, via at least one electrode of the plurality of first electrodes of the first endovascular device within the first blood vessel or the plurality of second electrodes of the second endovascular device within the second blood vessel, an electrical signal, wherein transmitting the electrical stimulation comprises passing electrical currents along a plurality of pathways between the first and second endovascular devices, wherein the plurality of first electrodes comprises X number of electrodes, the plurality of second electrodes comprises Y number of electrodes, and a number of available pathways between the plurality of first electrodes and the plurality of second electrodes is 2XY, wherein passing electrical currents along the plurality of pathways comprises passing electrical currents along more than half of the 2XY available pathways during the treatment cycle, and wherein X and Y are each greater than 10.

2. The method of claim 1, wherein at least one of the first blood vessel or the second blood vessel has an internal diameter of about 1 millimeters (mm) to about 5 mm.

3. The method of claim 2, wherein the internal diameter is about 2 millimeters (mm) to about 4 mm.

4. The method of claim 1, wherein at least one of the first blood vessel or the second blood vessel is a cerebral artery.

5. The method of claim 1, wherein at least one of the first blood vessel or the second blood vessel comprises a branch of one of: an internal carotid artery, an external carotid artery, a maxillary artery, a meningeal artery, or a vertebral artery of the patient.

6. The method of claim 1, wherein at least one of the first blood vessel or the second blood vessel is a vein.

7. The method of claim 1, wherein the plurality of first electrodes and the plurality of second electrodes are positioned on opposite sides of the target brain tissue site.

8. The method of claim 1, wherein the target brain tissue site comprises brain tissue in at least one of an anterior thalamus, a ventrolateral thalamus, or a subthalamic nucleus of a brain of the patient.

9. The method of claim 1, wherein the target brain tissue site comprises brain tissue in at least one of an internal segment of a globus pallidus, an external segment of the globus pallidus, a substantia nigra pars reticulata, a neostriatum, a cingulate, or a cingulate gyrus of a brain of the patient.

10. The method of claim 1, wherein the target brain tissue site comprises brain tissue in a cortex of a brain of the patient.

11. The method of claim 1, wherein at least some electrodes of at least one of the plurality of first electrodes or the plurality of second electrodes extend partially circumferentially around a longitudinal axis of the respective first or second endovascular device.

12. The method of claim 1, wherein at least some electrodes of at least one of the plurality of first electrodes or the plurality of second electrodes extend completely circumferentially around a longitudinal axis of the respective first or second endovascular device.

13. The method of claim 1, wherein transmitting the electrical stimulation along the plurality of pathways comprises passing electrical currents along the plurality of pathways, the plurality of pathways being between the plurality of first electrodes and the plurality of second electrodes.

14. The method of claim 1, wherein transmitting the electrical stimulation along the plurality of pathways comprises passing electrical currents along the plurality of pathways, the plurality of pathways being between groups of electrodes, each of the groups of electrodes including one or more electrodes from each of the plurality of first electrodes and the plurality of second electrodes.

15. The method of claim 14, wherein passing electrical currents along the plurality of pathways comprises sequentially delivering electrical current between different groups of electrodes during the treatment cycle.

16. The method of claim 14, wherein passing electrical currents along the plurality of pathways comprises simultaneously delivering electrical current between the groups of electrodes during the treatment cycle.

17. The method of claim 14, wherein the groups of electrodes include:

a first group including a distal-most electrode of the plurality of second electrodes and a proximal-most electrode of the plurality of first electrodes, wherein passing electrical currents along the plurality of pathways comprises passing electrical current along a first pathway between the distal-most electrode of the plurality of second electrodes and the proximal-most electrode of the plurality of first electrodes, the first pathway traversing both longitudinally and laterally through brain tissue from the second endovascular device to the first endovascular device; and a second group including electrodes that are longitudinally closer to each other than the distal-most electrode of the plurality of second electrodes and the proximal-most electrode of the plurality of first electrodes, wherein passing electrical currents along the plurality of pathways comprises passing electrical current along a second pathway between the electrodes of the second group.

18. The method of claim 1, further comprising switching a polarity of at least one of the conduction pathways between the plurality of first electrodes and the plurality of second electrodes at least once.

19. The method of claim 1, wherein at least one electrode of the plurality of first electrodes or the plurality of second electrodes is radially expandable.

20. The method of claim 1, wherein transmitting the electrical stimulation to the target brain tissue site comprises transmitting the electrical stimulation in conjunction with a treatment for at least one of stroke, atherosclerosis, vasoconstriction, artery dissection, vasculopathy, Moyamoya disease, fibromuscular dysplasia, arterial embolus, or intracerebral hemorrhage.

21. The method of claim 1, wherein transmitting the electrical stimulation to the target brain tissue site comprises transmitting the electrical stimulation in conjunction with a treatment for at least one of deep vein thrombosis, pulmonary embolism, or myocardial infarction.

22. The method of claim 1, wherein the electrical stimulation is configured to enhance drug delivery through electropermeation of barrier tight junctions.

23. The method of claim 1, wherein the electrical stimulation is configured to electrically stimulate undifferentiated stem cells and induce potentiation to neurons.

24. The method of claim 1, wherein the electrical stimulation is configured to cause implanted pluripotent stem cells or previously cultured neurons to populate and connect into functioning neural networks.

25. The method of claim 1, wherein the electrical stimulation is configured to at least one of enhance regeneration of cerebral neurocytes; inhibit or reverse formation of neurofibrillary tangles; inhibit or reverse formation of amyloid plaques; inhibit or reverse attachment of amyloid plaques to neurocytes; inhibit cellular apoptosis cascade associated with ischemic stroke; stimulate myelin sheath repair or formation; or increase rate and volume of pharmacologic agent delivery.

26. The method of claim 1, wherein passing electrical currents along the plurality of pathways comprises passing electrical currents along all of the 2XY available pathways during the treatment cycle.

27. A method comprising:

delivering, by a medical device and via a plurality of first electrodes of a first endovascular device within a first cerebral blood vessel and a plurality of second electrodes of a second endovascular device within a second cerebral blood vessel, electrical stimulation to brain tissue of a patient during a treatment cycle, wherein delivering the electrical stimulation comprises passing electrical currents along a plurality of pathways between the plurality of first electrodes and the plurality of second electrodes to establish a plurality of conduction pathways through the brain tissue, and wherein conduction pathways of the plurality of conduction pathways are more concentrated in some regions of the brain tissue between the first and second plurality of electrodes through which at least some conduction pathways traverse relative to other regions of the brain tissue between the first and second plurality of electrodes through which at least some conduction pathways traverse, wherein the plurality of first electrodes comprises X number of electrodes, the plurality of second electrodes comprises Y number of electrodes, and a number of available pathways between the plurality of first electrodes and the plurality of second electrodes is 2XY, wherein passing electrical currents along the plurality of pathways comprises passing electrical currents along more than half of the 2XY available pathways during the treatment cycle, and wherein X and Y are each greater than 10.

28. The method of claim 27, further comprising receiving an electrical signal via at least one electrode of the plurality of first electrodes within the first cerebral blood vessel.

29. The method of claim 27, wherein at least some electrodes of at least one of the plurality of first electrodes or the plurality of second electrodes extend partially circumferentially around a longitudinal axis of the respective first or second endovascular device.

30. The method of claim 27, wherein at least some electrodes of at least one of the plurality of first electrodes or the plurality of second electrodes extend completely circumferentially around a longitudinal axis of the respective first or second endovascular device.

31. The method of claim 27, wherein passing electrical currents along the plurality of pathways comprises passing electrical current along a first pathway between a distal-most electrode of the plurality of second electrodes and a proximal-most electrode of the plurality of first electrodes, the first pathway traversing both longitudinally and laterally through the brain tissue from the second endovascular device to the first endovascular device; and wherein passing electrical currents along the plurality of pathways comprises passing electrical current along a second pathway between electrodes that are longitudinally closer to each other than the distal-most electrode of the plurality of second electrodes and the proximal-most electrode of the plurality of first electrodes.

32. The method of claim 27, wherein at least one electrode of the plurality of first electrodes or the plurality of second electrodes is radially expandable.

33. The method of claim 27, wherein delivering the electrical stimulation comprises delivering the electrical stimulation in conjunction with a treatment for at least one of stroke, atherosclerosis, vasoconstriction, artery dissection, vasculopathy, Moyamoya disease, fibromuscular dysplasia, arterial embolus, or intracerebral hemorrhage.

34. The method of claim 27, wherein delivering the electrical stimulation to comprises delivering the electrical stimulation in conjunction with a treatment for at least one of deep vein thrombosis, pulmonary embolism, or myocardial infarction.

35. The method of claim 27, wherein passing electrical currents along the plurality of pathways between the plurality of first electrodes and the plurality of second electrodes to establish the plurality of conduction pathways through the brain tissue includes passing electrical currents along the plurality of pathways between the plurality of first electrodes and the plurality of second electrodes to establish a network of intersecting conduction pathways in the brain tissue.

36. A method comprising:

during a medical procedure, removing an obstruction in a blocked cerebral blood vessel of a patient to cause reperfusion of the cerebral blood vessel, the obstruction affecting a brain tissue site downstream of the obstruction by at least causing a neurological decline, by at least one of mechanical thrombectomy, aspiration, or drug therapy; and during the same medical procedure and following reperfusion of the cerebral blood vessel, delivering, via a plurality of first electrodes of a first endovascular device within vasculature downstream of a location of the obstruction and a plurality of second electrodes of a second endovascular device within the vasculature downstream of the location of the obstruction, electrical stimulation to the brain tissue site affected by the obstruction of the patient during a treatment cycle, wherein delivering the electrical stimulation comprises passing electrical currents along a plurality of pathways between the plurality of first electrodes and the plurality of second electrodes to establish a plurality of conduction pathways through the brain tissue site to inhibit the neurological decline caused by the obstruction and to promote growth factors to stimulate cellular growth at the brain tissue site following reperfusion of the cerebral blood vessel, and wherein at least some conduction pathways of the plurality of conduction pathways intersect.

37. The method of claim 36, wherein removing the obstruction comprises introducing a catheter in the vasculature, the method further comprising introducing at least one of the first endovascular device or the second endovascular device into the vasculature through the catheter.

38. The method of claim 36, wherein at least one electrode of the at least one of the first endovascular device or the second endovascular device is radially expandable.

39. The method of claim 36, wherein removing the obstruction comprises restoring blood flow by at least delivering a stent retriever to the blocked cerebral blood vessel.

40. The method of claim 36, wherein prior to removing the obstruction, the obstruction at least partially blocks blood flow to at least a first blood vessel branch and a second blood vessel branch, and wherein during delivery of electrical stimulation via the plurality of first electrodes and the plurality of second electrodes, the first endovascular device is positioned in the first blood vessel branch and the second endovascular device is positioned in the second blood vessel branch.

41. The method of claim 36, wherein removing the obstruction comprises introducing a catheter in the vasculature and navigating the catheter proximate the obstruction, and wherein the method further comprises:

introducing, during the same medical procedure and after reperfusion of the cerebral blood vessel, both of the first endovascular device and the second endovascular device into the vasculature through the catheter.

42. A method comprising:

transmitting, via a plurality of first electrodes of a first endoluminal device within a first lumen proximate a target intracranial region of a patient or a plurality of second electrodes of a second endoluminal device within a second lumen proximate the target intracranial region, electrical stimulation along a plurality of conduction pathways that intersect each other to the target intracranial region during a treatment cycle to establish, during the treatment cycle, a network of the conduction pathways between the plurality of first electrodes and the plurality of second electrodes; and receiving, via at least one electrode of the plurality of first electrodes of the first endoluminal device within the first lumen or the plurality of second electrodes of the second endoluminal device within the second lumen, an electrical signal, wherein transmitting the electrical stimulation comprises passing electrical currents along a plurality of pathways between the first and second endoluminal devices, wherein the plurality of first electrodes comprises X number of electrodes, the plurality of second electrodes comprises Y number of electrodes, and a number of available pathways between the plurality of first electrodes and the plurality of second electrodes is 2XY, wherein passing electrical currents along the plurality of pathways comprises passing electrical currents along more than half of the 2XY available pathways during the treatment cycle, and wherein X and Y are each greater than 10.

43. The method of claim 42, wherein the electrical signal is configured to control permeability of tissue.

44. The method of claim 42, wherein at least one of the first lumen or the second lumen has an internal diameter of about 1 millimeters (mm) to about 5 mm.

45. The method of claim 42, wherein the target intracranial region comprises brain tissue in at least one of an anterior thalamus, a ventrolateral thalamus, a subthalamic nucleus, an internal segment of a globus pallidus, an external segment of the globus pallidus, a substantia nigra pars reticulata, a neostriatum, a cingulate, a cingulate gyrus, or a cortex of a brain of the patient.

* * * * *